United States Patent [19]

Middeldorp

[11] Patent Number: 5,965,353
[45] Date of Patent: Oct. 12, 1999

[54] EPSTEIN-BARR VIRUS PEPTIDES AND ANTIBODIES AGAINST THESE PEPTIDES

[75] Inventor: Jaap Michiel Middeldorp, Oss, Netherlands

[73] Assignee: Akzo Nobel N.V., Arnhem, Netherlands

[21] Appl. No.: 08/240,717

[22] PCT Filed: Sep. 13, 1993

[86] PCT No.: PCT/EP93/02478

§ 371 Date: May 11, 1994

§ 102(e) Date: May 11, 1994

[87] PCT Pub. No.: WO94/06912

PCT Pub. Date: Mar. 31, 1994

[30] Foreign Application Priority Data

Sep. 14, 1992 [EP] European Pat. Off. .............. 92202797

[51] Int. Cl.[6] .............................. C12Q 1/70; C12N 5/20; C07K 14/05; C07K 16/08
[52] U.S. Cl. .............................. 435/5; 435/339; 530/324; 530/325; 530/327; 530/350; 530/387.9; 530/388.3; 530/389.4; 530/391.1
[58] Field of Search .................................. 435/5, 240.27, 435/339; 530/350, 387.9, 388.3, 389.4, 391.1, 324, 325, 327

[56] References Cited

U.S. PATENT DOCUMENTS

5,374,520 12/1994 Milman ........................................ 435/5

FOREIGN PATENT DOCUMENTS

| A-14809/92 | 10/1992 | Australia . |
| 0 508 427 | 10/1992 | European Pat. Off. . |
| WOA 8 601 210 | 2/1986 | WIPO . |
| WO90/01495 | 2/1990 | WIPO . |

OTHER PUBLICATIONS

Petersen et al., Human T Cell Responses to the Epstein–Barr Nuclear Antigen–1 (EBNA–1) as Evaluated by Synthetic Peptides, Cellular Immunology 123:325–333, 1989.

Orlowski et al., Inhibition of Specific Binding of EBNA 1 to DNA by Murine Monoclonal and Certain Human Polyclonal Antibodies, Virology 176:638–642, 1990.

Milman et al., Carboxyl–terminal domain of the Epstein––Barr virus nuclear antigen is highly immunogenic in man, Proc. Natl. Acad. Sci. USA 82:6300–6304, 1985.

Hammerskjold et al., "High–level expression of the Epstein––Barr virus EBNA–1 protein in CV1 cells and human lymphoid cells using a SV40 late replacement vector," Gene, vol. 43, No. 1–2, 1986, pp. 41–50, The Netherlands.

Yates et al., "Stable replication of plasmids derived from Epstein–Barr virus in various mammalian cells," Nature, vol. 313, pp. 812–815, Feb. 28, 1985, UK.

*Primary Examiner*—Marian C. Knode
*Assistant Examiner*—Donna C. Wortman
*Attorney, Agent, or Firm*—Mary E. Gormley

[57] ABSTRACT

The invention relates to a peptide or fragment thereof which is immunochemically reactive with Epstein-Barr Virus (EBV) antibodies. A new monoclonal antibody directed to said peptide or fragment thereof is also part of the invention. The invention also relates to a method for the detection of EBV or anti-EBV antibodies in a test fluid and also to an immunochemical reagent comprising a peptide, a fragment or a polypeptide according to the invention and a test kit to be used when applying the said detection methods. Detection of EBV in a test fluid or tissue specimen using antibodies, monoclonal and polyclonal; directed to the said peptide, which have the characteristics of detecting both native and denatured intact, functional EBNA-1 protein is also part of said invention.

15 Claims, 9 Drawing Sheets

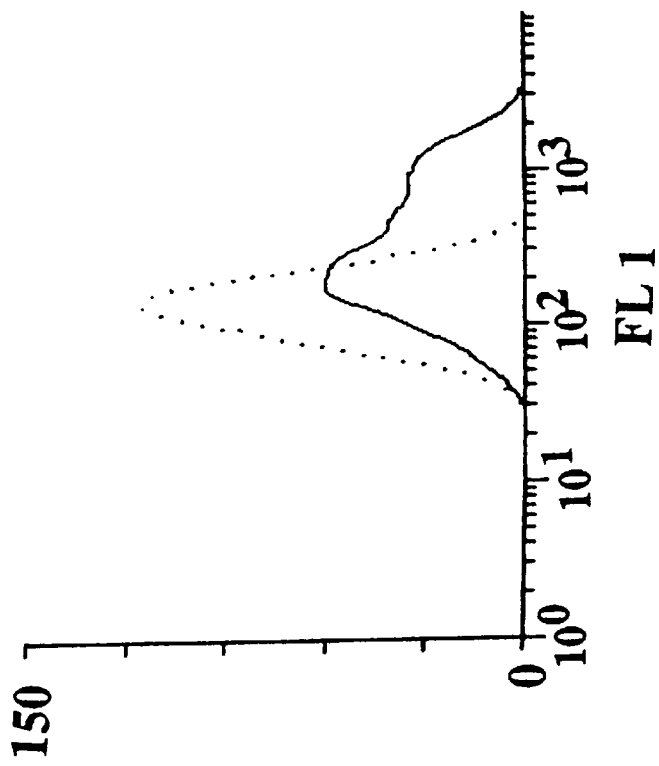
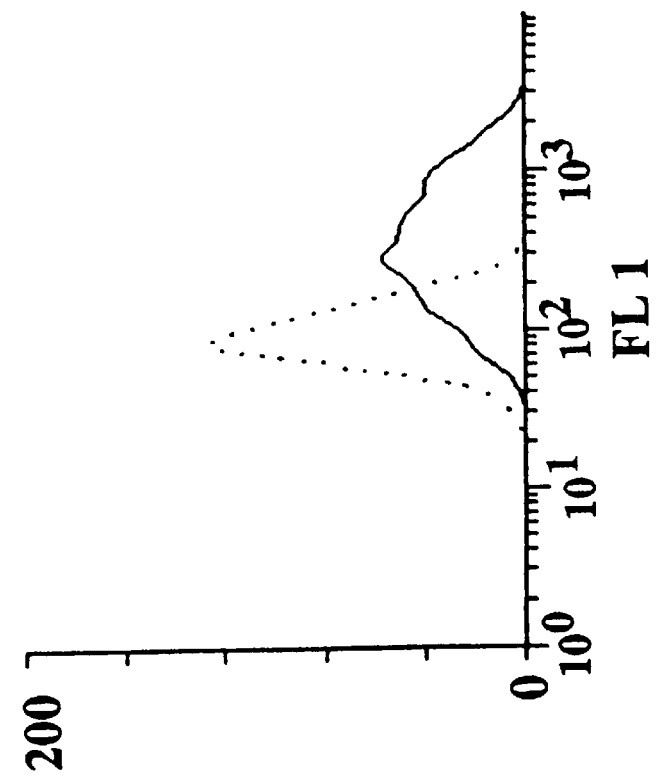

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 123 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Gly Gly Ser Gly Gly Arg Arg Gly Arg Gly Arg Glu Arg Ala Arg Gly
   1               5                   10                  15

Gly Ser Arg Glu Arg Ala Arg Gly Arg Gly Arg Gly Arg Gly Glu Lys
                   20                  25                  30

Arg Pro Arg Ser Pro Ser Ser Gln Ser Ser Ser Gly Ser Pro Pro
           35                  40                  45

Arg Arg Pro Pro Pro Gly Arg Arg Pro Phe Phe His Pro Val Gly Glu
           50                  55                  60

Ala Asp Tyr Phe Glu Tyr His Gln Glu Gly Gly Pro Asp Gly Glu Pro
   65                  70                  75                  80

Asp Val Pro Pro Gly Ala Ile Glu Gln Gly Pro Ala Asp Asp Pro Gly
                   85                  90                  95

Glu Gly Pro Ser Thr Gly Pro Arg Gly Gln Gly Asp Gly Gly Arg Arg
                   100                 105                 110

Lys Lys Gly Gly Trp Phe Gly Lys His Arg Gly
                   115                 120

(2) INFORMATION FOR SEQ ID NO:2:

(i) SEQUENCE CHARACTERISTICS:
       (A) LENGTH: 20 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Arg Ala Arg Gly Arg Gly Arg Gly Arg Gly Glu Lys Arg Pro Arg Ser
   1               5                   10                  15

Pro Ser Ser Gln
                   20

(2) INFORMATION FOR SEQ ID NO:3:

(i) SEQUENCE CHARACTERISTICS:
       (A) LENGTH: 27 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

Pro Pro Arg Arg Pro Pro Pro Gly Arg Arg Pro Phe Phe His Pro Val
   1               5                   10                  15

Gly Glu Ala Asp Tyr Phe Glu Tyr His Gln Glu

-continued

```
            20              25
```

(2) INFORMATION FOR SEQ ID NO:4:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Asp Gly Glu Pro Asp Val Pro Pro Gly Ala Ile Glu Gln Gly Pro Ala
1               5                   10                  15

Asp Asp Pro Gly Glu Gly Pro Ser Thr Gly Pro Arg Gly
            20              25
```

(2) INFORMATION FOR SEQ ID NO:5:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Pro Pro Arg Arg Pro Pro Pro Gly Arg Arg Pro Phe Phe His Pro Val
1               5                   10                  15

Gly Glu Ala Asp Tyr Phe Glu Tyr His Gln Glu Cys Cys Asp Gly Glu
            20                  25                  30

Pro Asp Val Pro Pro Gly Ala Ile Glu Gln Gly Pro Ala Asp Asp Pro
                35                  40                  45

Gly Glu Gly Pro Ser Thr Gly Pro Arg Gly
        50                  55
```

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Pro Gly Ala Ile Glu Gln Gly Pro Ala
1               5
```

EPSTEIN-BARR VIRUS PEPTIDES AND ANTIBODIES AGAINST THESE PEPTIDES

FIELD OF THE INVENTION

The present invention relates to peptides immunochemically reactive with antibodies to the Epstein-Barr virus (EBV), monoclonal antibodies against these peptides, cell lines capable of producing monoclonal antibodies and anti-idiotype antibodies. The invention is further concerned with immunological reagents and methods for the detection of EBV or anti-EBV antibodies.

BACKGROUND OF THE INVENTION

EBV is an ubiquitous human herpes virus that was first discovered in association with the African (endemic or e) form of Burkitt's lymphoma (BL). Subsequently the virus was also found associated with nasopharyngeal carcinoma (NPC) and was shown to be the causative agent of infectious mononucleosis (IM). Infection usually occurs during early childhood, generally resulting in a subclinical manifestation, occasionally with mild symptoms. Infection during adolescence or adulthood, however, can give rise to IM characterized by the presence of atypical lymphocytes in the periphery. The bulk of these lymphocytes are T lymphocytes; however, included in their number are a small population of B lymphocytes infected by EBV. The infection of B lymphocytes may also be accomplished in vitro. Such cells become transformed and proliferate indefinitely in culture and have been referred to as "immortalized", "latently infected" or "growth transformed". As far as is known, all individuals who become infected with EBV remain latently infected for life. This is reflected by the lifelong continuous presence of small numbers of EBV-genome positive transformed B-cells among the circulating peripheral blood lymphocytes and the continual but periodic shedding of virus in the oropharynx.

In the vast majority of cases EBV infection results in a lymphoproliferative disease that may be temporarily debilitating, but is always benign and self-limiting. In certain immunosuppressed individuals, however, the result can be full-blown malignancy. This occurs in individuals who are immuno-suppressed intentionally, particularly children receiving organ transplants who are treated with cyclosporine A, or opportunistically, as in the case with individuals infected with HIV, or genetically, as in the case of affected males carrying the XLP (x-linked lymphoproliferative syndrome) gene. In these cases the resulting malignancies derive from the polyclonal proliferation of EBV-infected B cells. In addition, in such patients uncontrolled epithelial replication of the virus is detectable in lesions of oral hairy leukoplakia. Thus, the immune response plays a central role in the control of EBV infection.

The presence of EBV in cells or tissues can be demonstrated by detection of the viral genome or demonstration of the EBNA-1 protein, the sole latency associated protein product that is universally expressed in EBV-infected cells.

As mentioned above EBV is a member of the herpesviruses. It possesses the following structural properties:

The EBV genome consists of a linear double stranded DNA molecule (172,000 basepairs).

The virion consists of a core (proteins and DNA), surrounded by an icosahedral capsid, and a membrane envelope enclosing the capsid. The icosahedral capsid is built up of hexameric and pentameric capsomeres. The membrane envelope consists of a protein/lipid bilayer membrane with spikes on its outer surface. The space between the capsid shell and the envelope is filled with amorphous protein, called the tegument.

Like all herpesviruses, EBV is capable of establishing a latent life-long infection in its host subsequent to primary infection. This latency represents a perfect balance between EBV and its human host, controlled by the hosts immune system.

To date most biochemical and biological studies have been performed on three prototype strains of EBV, being B95-8 (transforming virus produced in a marmoset cell line), P3HR1 (non-transforming virus produced by a Burkitt's lymphoma tumor cell line) and Raji (latent virus in a Burkitt's lymphoma tumor cell line).

During the last few years the entire DNA sequence of prototype virus strain, B95-8, has been determined. Analysis of this sequence has resulted in the identification of more than 80 open reading frames (Baer et al., 1984, Nature 310, p. 207–211).

The biology of EBV poses a special problem to investigators because its biological characteristics (latent infection) do not lend itself to the classic virus analysis. Furthermore, its cell and host range are effectively limited to human (and those of a few higher primates) B-lymphocytes and epithelial cells which are generally not amenable to culture in vitro. In addition, the absence of a fully permissive cell type, one in which the virus lytically replicates, has severely limited the ability to produce large amounts of the virus.

DNA molecules of B95-8, P3HR1— and Raji-isolates have been the prototypes for detailed restriction endonuclease mapping, and for cloning into *Escherichia coli* (*E.coli*) plasmids and in bacteriophage lambda, and for nucleotide sequencing.

The EBV genome consists of a single double stranded DNA molecule made up of unique and tandemly repeated DNA elements. Each end of the DNA molecule contains multiple terminal sequences which permit covalently linking and circularization of the genome. In virus particles the EBV-genome is only detectable in a linear form. On the contrary, it exists as a circular episome inside the nucleus of latently infected cells, and occasionally becomes integrated into the host cell chromosomes.

The internal repeat sequences, IR1 to IR4, separate the EBV-genome into 5 unique regions. The U2 and U3 regions vary extensively among different EBV isolates and, the former being almost entirely deleted in the P3HR-1 strain of EBV.

The nomenclature for EBV reading frames is based on their position in the virus genome. The names begins with the initials of the BamH1 or EcoR1 restriction fragment where expression begins. The third letter in the name is L or R, depending or whether the expression is leftward or rightward on the standard map. (So BLLF2 is the second leftward reading frame starting in BamH1 restriction fragment L.).

The serological classification of virus antigens in the production cycle of EBV is based on different fluorescence techniques.

Antigens specifically detected by means of the anti-complement immunofluorescence technique in the nucleus of fixed latently infected B-cells (e.g. Raji-cells) are classified as Epstein-Barr nuclear antigens (EBNA).

Upon activation of viral gene expression by chemical or viral factors a class of early antigens (EA) is detected whose synthesis is not blocked by inhibition of viral DNA synthesis. Dependent on the type of fixative used (Methanol or Acetone) two distinct sets of EA are detectable, $EA_R$ and EA$_D$. EA is detectable by indirect immunofluorescence in the cytoplasm and nucleus of induced cells. Following onset of viral DNA-synthesis (and depending upon it) virus structural proteins (VCA) are synthesized which are detectable by indirect immunofluorescence in the cytoplasm and nucleus of virus producer cells (e.g. P$_3$HR$_1$ cells). On the surface of viable infected cells, induced for virus production a set of antigens (MA) is detectable by indirect immunofluorescence. These antigens can also be found on the viral envelope and are important targets for virus neutralization.

Detection of EBV-specific antibodies in human sera can routinely be performed by serological techniques as described by Heule and Heule (Human Pathology, 5, 551–565, 1974).

Based upon biochemical and immunofluorescence data it is possible to distinguish five different classes of antigen molecules. The different viral polypeptides are designated by their molecular weight, and no common nomenclature has been established for all EBV proteins in order to allow their unique description.

The five different groups of antigens are:

A. The group of antigens which are expressed during a state of latency (EBNAs and LMPs).

B. The group of antigens which are responsible for genome activation and initial induction of viral replication (IEA).

C. The group of antigens which are induced by IEA-gene products and which are required for replication of viral DNA; these antigens are mostly viral enzymes (EA).

D. The group of antigens which are structural components of the viral particle and are expressed late in the viral replication cycle (VCA), after initiation of viral DNA-synthesis.

E. The group of antigens which are expressed in the cell membrane of the infected cell (MA).

Epstein-Barr nuclear antigens (EBNA)

The Epstein Barr Nuclear Antigen 1 (EBNA-1), encoded in the BKRF 1, reading frame, is the only EBV-encoded protein expressed universally in all latently infected and tumor-associated cells in vivo and in vitro and forms an important target molecule for studying the mechanisms of DNA replication and gene activation.

EBNA-1 was identified by immunoblotting and radioimmunoelectrophoresis in EBV-positive but not in three EBV-negative cell lines, utilizing four EBV-positive human sera in comparison with two EBV-negative human sera. The antigens identified had different molecular weights in the different cell lines analyzed, ranging from 65,000 to 73,000. A complement-fixing antigen had been partially purified more than 200 times and was found to co-purify with the 65-kDa EBNA identified by immunoblotting. Since EBNA is defined by anti-complement immunofluorescence (ACIF), it was suggested that the 65-kDa antigen was a major component of EBNA.

The EBNA gene was mapped by transfecting mouse cells with the cloned BamHI K restriction enzyme fragment of EBV DNA. The transfection of a mouse fibroblast line with this fragment, together with a dominant selectable marker, led to the stable expression of a nuclear antigen identified in ACIF with EBNA-positive, but not EBNA-negative human sera. In a subsequent study it was found that Bam K-transfected cells expressed a 78-kDa polypeptide that co-migrated with the EBNA-1 polypeptide of B95-8 cells.

More recent studies have revealed an immunodominant region within the glycine-alanine repeat region, usually referred to as p62 or p107, which is strongly reactive with human sera. This gly—ala fragment however was shown to be contained within normal human proteins and was found to be the target for auto-antibodies. In addition, further studies have revealed that especially IgM antibodies in the sera from patients with active CMV, HSV or Toxoplasma infections occasionally show cross-reactivity with this peptide. Furthermore a C-terminal fragment of 28 kD, encoding AA 461–641 of EBNA-1, expressed in *E.coli* was shown to be reactive with human serum antibodies. Additional studies, thus far, have failed to identify fragments of the EBNA-1 protein that can be used for replacing the intact EBNA-1 protein in diagnostics.

The molecular size of EBNA-1 can be used for strain identification (EBNO-typing) as the size of the gly—ala repeat region may show significant variation among individual viral strains.

EBNA-1 has been detected immunologically in cells of Burkitt lymphoma, Nasopharyngeal carcinoma and Reed-Sternberg cells as found in Hodgkin's Disease.

In addition, EBNA has also been detected in polyclonal lympho-proliferative lesions in transplants and AIDS-patients and is the earliest marker for identification of B-lymphocytes in cell culture.

Several functional domains have been identified on the EBNA-1 molecule, such as the DNA-binding (Ori-P) domain, nuclear localization domain, the transactivation domain, the DNA-looping domain and the dimerization domain. EBNA-1 exerts its DNA binding function as a homo dimeric molecule.

At present EBV-specific serodiagnosis is accomplished by rather subjective immunofluorescence tests. Progress to more simple and uniform diagnosis (e.g. ELISA) is hampered because bulk production and purification of viral antigens are not possible using standard virus-producing cell lines.

The only way to achieve this would be to use alternatively prepared EBV antigen(s). These EBV antigens could be prepared with either genetic engineering techniques or synthetic peptide techniques.

For the development of a specific and sensitive method to enable a reliable diagnosis to be made in various phases of the infection with EBV it is of great importance to identify immunodominant viral proteins and epitopes thereof.

SUMMARY OF THE INVENTION

The present invention provides peptides, immunochemically reactive with antibodies to the Epstein-Barr Virus, comprising at least part of the amino acid sequence as shown in SEQ ID No.: 1.

A peptide having the amino acid sequence as shown in SEQ ID No:1 and fragments thereof are therefore part of the present invention.

DETAILED DESCRIPTION OF THE INVENTION

The peptides according to the invention are found to be particularly suitable for use in a diagnostic method for the determination of the presence of EBV or EBV-antibodies in a sample. Moreover, a peptide according to the invention may be used in suitable pharmaceutical dosage forms in the treatment of an EBV-related disease. The preparation of vaccines thus obtained which contain a peptide or fragment thereof as active ingredients, is known to one skilled in the art.

In contrast to the natural EBV, the peptides according to the invention have the great advantage that they are of a safe non-infectious origin.

The invention also comprises fragments of said peptides which are still immunochemically reactive with antibodies to the Epstein-Barr Virus.

The specific characteristics of the said peptide region of EBNA-1 make it accessible to antibodies in both native and denatured configurations of the EBNA-1 protein.

The term "peptide" as used herein refers to a molecular chain of amino acids with a biological activity, and does not refer to a specific length of the product. Thus inter alia, proteins, fusion proteins or fusion peptides, oligopeptides and polypeptides are included. If required peptides according to the invention can be modified in vivo or in vitro, for example by glycosylation, amidation, carboxylation or phosphorylation. Functional variants like, for example, acid addition salts, amides, esters, and specifically C-terminal esters, and N-acyl derivatives of the peptides according to the invention are therefore also considered part of the present invention. It will be understood that for the particular proteins or polypeptides embraced herein, natural variations can also exist. These variations may be demonstrated by (an) amino acid difference(s) in the overall sequence or by deletions, substitutions, insertions, inversions or additions of (an) amino acid(s) in said sequence. Amino acid substitutions from which can be expected that they do not essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science 227, 1435–1441, 1985) and determining the functional similarity between homologous proteins.

The term "fragment" as used herein means an amino acid sequence comprising a subsequence of a peptide of the invention. Said fragment is a peptide having one or more immunogenic determinants of the EBNA-1 protein. Fragments can inter alia be produced by enzymatic cleavage of precursor molecules, using restriction endonucleases for the DNA and proteases for the polypeptides. Other methods include chemical synthesis of the fragments or the expression of peptide fragments by DNA fragments.

Suitable immunogenic fragments of a peptide according to the invention containing (an) epitope(s) can be found by means of the method described in Patent Application WO 86/06487, Geysen, H. M. et al. (Proc. Natl. Acad. Sci. 81, 3998–4002, 1984), Geysen, H. M. et al. (J. Immunol. Meth. 102, 259–274, 1987) based on the pepscan method, wherein a series of partially overlapping peptides corresponding with partial sequences of the complete polypeptide under consideration, are synthesized and their reactivity with antibodies is investigated.

In addition, a number of regions of the peptides can be designated epitopes on the basis of theoretical considerations, although the predictive value of these theoretical considerations is limited. The determination of these regions is based on a combination of the hydrophilicity criteria according to Hopp and Woods (Proc. Natl. Acad. Sci. 78, 3824–3828, 1981) and the secondary structure aspects according to Chou and Fasman (Advances in Enzymology 47, 45–148, 1987).

Preferred peptides according to the invention are peptides comprising at least one of the sequences as depicted in SEQ ID No.: 2 to 6.

Peptides having the sequences as shown in SEQ ID No. 2–4 are fragments of the peptide with amino acid sequence as shown in SEQ ID No.1 and correspond to amino acids no. 368–387 [SEQ ID NO: 2], 394–420 [SEQ ID NO: 3] and 424–452 [SEQ ID NO: 4] of the EBNA-1 sequence respectively. A peptide having the amino acid sequence as shown in SEQ ID No.: 5 is a peptide comprising a combination of fragments (SEQ ID No.'s 2–4) of the sequence of SEQ ID No.: 1.

The preparation of the peptides or fragments thereof according to the invention is effected by means of one of the known organic chemical methods for peptide synthesis or with the aid of recombinant DNA techniques.

The organic chemical methods for peptide synthesis are considered to include the coupling of the required amino acids by means of a condensation reaction, either in homogeneous phase or with the aid of a solid phase.

The condensation reaction can be carried out as follows:

a) condensation of a compound (amino acid, peptide) with a free carboxyl group and protected other reactive groups with a compound (amino acid, peptide) with a free amino group and protected other reactive groups, in the presence of a condensation agent;

b) condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester.

The most common methods for the above condensation reactions are: the carbodiimide method, the azide method, the mixed anhydride method and the method using activated esters, such as described in The Peptides, Analysis, Synthesis, Biology Vol. 1–3 (Ed. Gross, E. and Meienhofer, J.) 1979, 1980, 1981 (Academic Press, Inc.).

Preparation of suitable fragments of above-mentioned peptides according to the invention using the "solid phase" is for instance described in J. Amer. Chem. Soc. 85, 2149 (1963) and Int. J. Peptide Protein Res. 35, 161–214 (1990). The coupling of the amino acids of the peptide to be prepared usually starts from the carboxyl end side. For this method a solid phase is needed on which there are reactive groups or on which such groups can be introduced. This can be, for example, a copolymer of benzene and divinylbenzene with reactive chloromethyl groups, or a polymeric solid phase rendered reactive with hydroxymethyl or amine-function.

A particulary suitable solid phase is, for example, the p-alkoxybenzyl alcohol resin (4-hydroxy-methyl-phenoxy-methyl-copolystrene-1% divinylbenzene resin), described by Wang (1974) J. Am. Chem. Soc. 95, 1328. After synthesis the peptides can be split from this solid phase under mild conditions.

After synthesis of the desired amino acid sequence, detaching of the peptide from the resin follows, for example, with trifluoromethanesulphonic acid or with methanesulphonic acid dissolved in trifluoroacetic acid. The peptide can also be removed from the carrier by transesterification with a lower alcohol, preferably methanol or ethanol, in which case a lower alkyl ester of the peptide is formed directly. Likewise, splitting with the aid of ammonia gives the amide of a peptide according to the invention.

The reactive groups which may not participate in the condensation reaction are, as stated, effectively protected by groups which can be removed again very easily by hydrolysis with the aid of acid, base or reduction. Thus, a carboxyl group can be effectively protected by, for example, esterification with methanol, ethanol, tertiary butanol, benzyl alcohol or p-nitrobenzyl alcohol and amines linked to solid support.

Groups which can effectively protect an amino group are the ethoxycarbonyl, benzyloxycarbonyl, t-butoxy-carbonyl (t-boc) or p-methoxy-benzyloxycarbonyl group, or an acid group derived from a sulphonic acid, such as the benzene-sulphonyl or p-toluene-sulphonyl group, but other groups can also be used, such as substituted or unsubstituted aryl or aralkyl groups, for example benzyl and triphenylmethyl, or groups such as ortho-nitrophenyl-sulphenyl and 2-benzoyl-1-methyl-vinyl. A particularly suitable α-amino-protective group is, for example, the base-sensitive 9-fluorenyl-methoxycarbonyl (Fmoc) group [Carpino & Han (1970) J. Amer. Chem. Soc. 92, 5748].

A more extensive account of possible protecting groups can be found in The Peptides, Analysis, Synthesis, Biology, Vol. 1–9 (Eds. Gross, Udenfriend and Meienhofer) 1979–1987 (Academic Press, Inc.).

It is necessary also to protect the ε-amino group of lysine and advisable for the guanidine group of arginine. Customary protective groups in this connection are a Boc-group for lysine and a Pmc- or Pms- or Mbs-group or Mtr-group for arginine.

The protective groups can be split off by various conventional methods, depending on the nature of the particular group, for example with the aid of trifluoroacetic acid or by mild reduction, for example with hydrogen and a catalyst, such as palladium, or with HBr in glacial acetic acid.

As already indicated above, the peptides according to the invention can likewise be prepared with the aid of recombinant DNA techniques. This possibility is of importance particularly when the peptide is incorporated in a repeating sequence ("in tandem") or when the peptide can be prepared as a constituent of a (much larger) protein or polypeptide or as a fusion protein with, for example, (part of) β-galactosidase. This type of peptides therefore likewise falls within the scope of the invention. For this purpose, as a constituent of a recombinant DNA, a nucleic acid sequence is used which codes for a peptide according to the invention and which, furthermore, is substantially free from nucleic acid segments, which in the naturally occurring EBV genome flank the nucleic acid sequence indicated above.

This latter method involves the preparation of the desired peptide by means of bringing to expression a recombinant polynucleotide with a nucleic acid sequence which is coding for one or more of the peptides in question in a suitable microorganism as host.

A nucleic acid sequence encoding a peptide according to the present invention can be ligated to various replication effecting DNA sequences with which it is not associated or linked in nature resulting in a recombinant vector molecule which can be used for the transformation of a suitable host. Useful recombinant vector molecules, are preferably derived from, for example plasmids, bacteriophages, cosmids or viruses.

Specific vectors or cloning vehicles which can be used to clone nucleic acid sequences are known in the art and include inter alia plasmid vectors such as pBR322, the various pUC, pGEM and Bluescript plasmids, bacteriophages, e.g. kgt-Wes, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., Arch. Virol. 110, 124, 1990). The methods to be used for the construction of a recombinant vector molecule are known to those of ordinarily skill in the art and are inter alia set forth in Maniatis, T. et al. (Molecular Cloning A Laboratory Manual, second edition; Cold Spring Harbor Laboratory, 1989).

For example, the insertion of the nucleic acid sequence encoding a peptide according to the invention into a cloning vector can easily be achieved when both the genes and the desired cloning vehicle have been cut with the same restriction enzyme(s) as complementary DNA termini are thereby produced.

The recombinant vector molecules may additionally contain one or more marker activities that may be used to select for desired transformants, such as ampicillin and tetracycline resistance in pBR322, as for example ampicillin resistance and α-peptide of β-galactosidase in pUC8.

It should, of course, be understood that the nucleotide sequences inserted at the selected site of the cloning vector may include only a fragment of the complete nucleic acid sequence encoding for the peptides according to the invention as long as the transformed host will produce a polypeptide having at least one or more immunogenic determinants.

Antibodies, directed to a peptide according to the invention, are also part of the present invention.

The peptides or fragments thereof prepared and described above can be used to produce antibodies, both polyclonal and monoclonal. Monoclonal antibodies directed against peptides according to the invention can be readily produced by one skilled in the art.

Prior to the present invention there has been no report of antibodies generated against this specific peptide fragment of EBNA-1. No one skilled in the art till this moment has known the availability of the epitopes to bind antibodies.

The monoclonal antibodies according to the present invention, therefore, provide a new means for the diagnosis of EBV infection.

Preferred antibodies according to the invention are monoclonal antibody having the same reactivity with EBNA-1 as monoclonal antibodies produced by the hybridoma cell line deposited with the European Collection of Animal Cell Cultures (ECACC), Porton Down (UK), under deposit No. 92071613 Jul. 16, 1992.

A new (monoclonal) antibody according to the invention, which are designated as EBNA.OT1x, was generated by immunizing mice with Baculovirus-derived EBNA-1 protein lacking the Gly—Ala repeat region. With deletion fragments from EBNA-1 expressed in E.coli the binding epitope of EBNA.OT1x was located within positions 430–438 [SEQ ID NO: 6], close to the putative nuclear localization signal EBNA.OT1x has been used in immunoprecipitation studies. EBNA.OT1x also binds to denatured EBNA-1 as used in Western blot studies and immunofluorescence on fixed permeabilized cells (FACS) using indirect detection techniques, and reacts with EBNA-1 from a wide variety of virus strains and virus-infected target cells. EBNA.OT1x binds to EBNA-1 from multiple EBV-isolates and can be used in immunohistochemical staining in a variety of human tumor tissues.

Immortalized cell lines capable of excreting monoclonal antibodies according to the invention are also part of the present invention.

The preparation of cell lines producing monoclonal antibodies may occur by, for example, by the Kohler and Milstein technique (Kohler and Milstein devised the techniques that resulted in the formation monoclonal antibody-producing hybridomas (G. Kohler and C. Milstein, 1975, Nature 256:495–497; 1976, Eur. J. Immunol. 6:511–519)), transformation with Epstein-Barr Virus, or a direct transformation technique of B-lymphocytes with oncogenic DNA, or a direct fusion of human B-lymphocytes with a fusion partner being either a human or a mouse-human hybrid myeloma cell line, or a direct fusion of an EBV-transformed B cell line with said myeloma cell lines.

A preferred cell line according to the invention is the cell line deposited at the European Collection of Animal Cell Cultures, Porton Down (UK) under deposit No. 92071613.

This hybridoma cell line was produced by the fusion of a myeloma cell with a lymphocyte derived from a mouse previously inoculated with an EBNA-1 peptide according to the invention. (A peptide with the amino acid sequence as shown in SEQ ID No.: 5.)

The invention further comprises the use of antibodies to said peptide in immunological and biochemical methods aiming to detect the full length protein in a test fluid or tissue specimen.

Up till now detection of EBNA-1 in EBV infected cells was performed by using the anti-complement immunofluorescence (ACIF) technique using human sera as the anti EBNA-1 antibody source. Indirect immunofluorescence techniques failed to detect EBNA-1 binding antibodies in human sera. ACIF is complicated by the extra complement-incubation step and the instability of the complement itself. In addition false-positive and -negative reactions are frequently encountered when reagents used for ACIF are not properly used.

The EBNA.OT1x antibody, on the other hand, eliminates these problems and allows the sensitive detection of EBNA-1 in a variety of EBV-infected cells by means of indirect immunofluorescence.

The presence of EBNA-1 in the cell nucleus is the hallmark of latent EBV-infection in cells, both in vivo and in vitro.

EBNA.OTx1 is capable of penetrating into cells thus allowing the detection of EBNA-1 intracellularly in EBV-infected cells: The EBV.OT1x antibody can be applied in Fluorescence Activated Cell Sorter (FACS) analysis of nuclear staining in EBV-infected cells permeabilized by buffered formalin-acetone (BFA) fixation as described by Slaper-Cortenbach et al. (Blood, 72, 1639–1644, 1988). This method has the advantage of being simple and rapid and allows the detection of EBV-infected B-lymphocytes cultured in vitro. This technology may also be applied to the detection and monitoring of EBV-associated lymphoproliferative diseases and lymphoma.

Antibodies, both monoclonal and polyclonal, directed against peptides according to the invention are very suitable in diagnosis and immunocytochemistry for detection in situ in tissue specimens, while those antibodies which are neutralizing are very useful in passive immunotherapy.

The antibodies according to the invention may also be used in EBNO-typing of different EBV isolates. As mentioned before, EBV isolates (strains) can be characterized by the molecular weight of the EBNA-1 molecule produced, due to the extensive variation in length of the glycine-alanine repeat region in this protein. Unlike previously described reagents, being mainly human sera, the EBNA.OT1x monoclonal antibody is a stable and reproducible reagent, detecting a binding epitope which is highly conserved within the EBV-family, which is highly suitable for EBNO-typing of EBV strains.

Part of the invention is also the "humanizing" of the monoclonal antibodies in question. Techniques for raising the "humanized" monoclonal antibodies are known in the art.

Especially monoclonal antibodies may be used to raise anti-idiotype antibodies. Techniques for raising anti-idiotype antibodies are known in the art.

Anti-idiotype antibodies reactive with the monoclonal antibodies according to the invention, as described above, are part of the present invention.

Anti-idiotype antibodies are antibodies directed to the variable part of immunoglobulins. A sub-population of anti-idiotype antibodies is known as "anti-idiotype β" or "internal images". These anti-idiotype β antibodies have either a structural or a three dimensional resemblance with the antigen (Uytdehaag, F. G. C. M. et al. Immunol.Rev; 90; 93–113; 1986). This type of anti-idiotype antibodies is widely used as a vaccine against infectious diseases in animal models (Hiernaux J. R.; Infect.Immun.; 56; 1407–1413; 1988, Kennedy, R. C. et al.; Science 232; 220–223;1986). For use in assays the anti-idiotype antibodies can be raised in large amounts.

Techniques for raising anti-idiotype antibodies are known in the art. For example, anti-idiotype antibodies according to the invention can be obtained by immunizing BALB/c mice with monoclonal antibodies, coupled to KLH with glutaraldehyde according to standard literature procedures, mixed with Freund's complete adjuvant. The spleen cells of these mice can be immortalized and the thus obtained hybridomas can be screened for anti-idiotype antibody production. Screening of the hybridomas can be performed, for example, by binding monoclonal antibodies according to the invention to a solid phase (wells of microtiter plates) and incubating the solid phase with culture supernatant of growing hybridomas. An EBV peptide coupled to Horseradish Peroxidase (HRP) can be added. The presence of anti-idiotype antibodies in culture supernatant will then be indicated by inhibition of the binding of this peptide conjugate to the monoclonal antibodies coated on the solid phase.

Anti-idiotype antibodies can be used for instance for inhibiting the binding of human and/or animal EBV-antigen in an immunoassay using EBV-antibodies. Alternatively anti-idiotype antibodies can be used as a mimicking agent of the immunochemical reagent mentioned hereunder.

Said anti-idiotype antibodies are also useful for diagnosis and treatment of EBV, as well as for the elucidation of important epitopic regions of EBV-antigens.

An immunochemical reagent comprising one or more peptides or antibodies according to the invention is also part of the present invention.

The term "immunochemical reagent" according to the invention usually consists of one more peptides according to the invention and a suitable support or a labelling substance.

Supports which can be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle, a carrier protein such as BSA or KLH.

Labelling substances which can be used are, inter alia, a radioactive isotope, a fluorescent compound, an enzyme, a dye sol, metal sol or metal compound as sol particle.

In a method for the detection of antibodies directed against EBV in a sample, an immuno-chemical reagent according to the invention is brought into contact with the sample. Thereafter which, the presence of immune complexes formed between the peptide and antibodies in the sample is detected and by this detection the presence of EBV antibodies in the sample is known and can be determined quantitatively.

Depending on the nature and further characteristics of the immunochemical reagent the immunochemical reaction that takes place is a sandwich reaction, an agglutination reaction, a competition reaction or an inhibition reaction.

For the detection of EBV in a sample an immunochemical reagent according to the invention, containing one or more peptides according to the invention, can be brought into contact with the sample and anti-EBV after which the presence of immune complexes formed can be detected and, from this, the presence of EBV in a sample can be determined.

A particularly suitable method for the detection of EBV in a sample is based on a competition reaction between a peptide according to the invention provided with a labelling substance and an EBV antigen (present in the sample) whereby the peptide and the antigen are competing with the antibody directed against EBV attached to a solid support.

The invention further comprises a method for the detection of Epstein-Barr virus in a sample characterized in that an antibody according to the invention is brought into contact with a sample whereafter the presence of immune complexes formed is detected which is a measure for the presence of Epstein-Barr Virus in the sample.

A test kit according to the invention comprises as an essential constituent an immunochemical reagent as described above. Carrying out a sandwich reaction, for the detection of EBV antibodies the test kit nay comprise, for example, the peptide according to the invention coated to a solid support, L or example the inner wall of a microtest well, and either a labelled peptide according to the invention or a labelled anti-antibody.

For carrying out a competition reaction, the test kit may comprise a peptide according to the invention coated to a solid support, and a labelled antibody directed against EBV preferably a monoclonal antibody directed against said peptide.

In an agglutination reaction the test kit comprises an immunochemical reagent which may comprise a peptide according to the invention coated to particles or sols.

Another embodiment of a test kit is, for example, the use of a labelled peptide according to the invention as immunochemical reagent in a competition reaction with an EBV antigen to be detected for a binding site on the antibody directed against EBV, which is coated to a solid support.

Line no.1 represents the immunoreactivity of an EBV negative human serum towards the respective 12-mer peptides.

Line no.2–6 represent the immunoreactivity of EBV positive human sera towards the 12-mer peptides.

Figure 2:
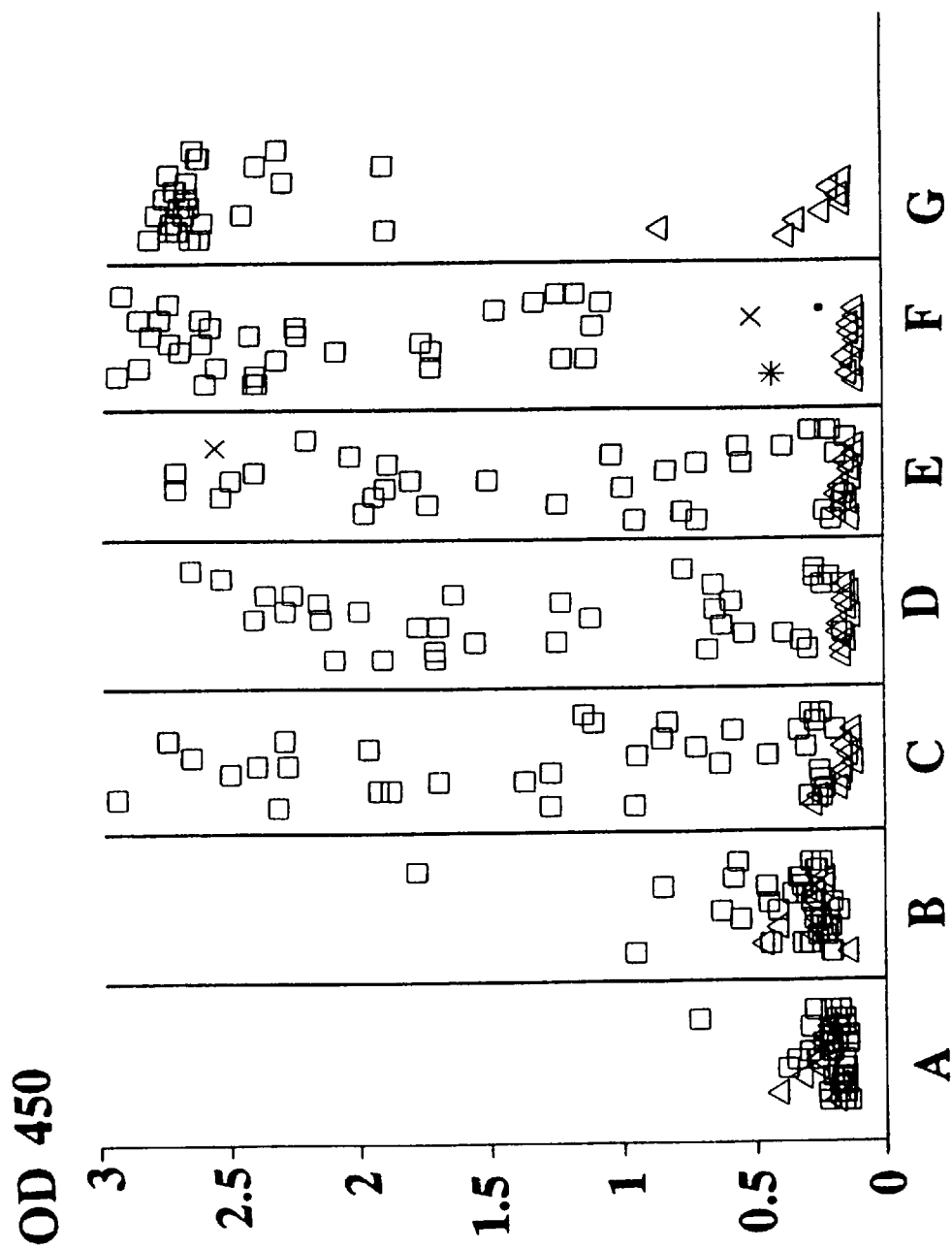

FIG. 2: ELISA reactivity (optical density at 450 nm) of 46 human serum samples tested for IgG-reactivity against selected synthetic peptides derived from the EBNA-1 protein.

Δ indicates sera negative by standard serological analysis

☐ indicates sera positive by standard serological analysis

× indicates sera positive on immunoblot for EBNA-1 only.

☐,* indicates sera with no detectable anti EBNA-1 antibodies by immunoblot but otherwise (i.e. anti-VCA) EBV-seropositive.

A=peptide 348–369

B=peptide 368–387 [SEQ ID NO:2]

C=peptide 394–420 [SEQ ID NO:3]

D=peptide 424–452 [SEQ ID NO:4]

E=peptide Gly—Ala

F=combi-peptide

G=EBNA-1 Baculo

Figure 3:
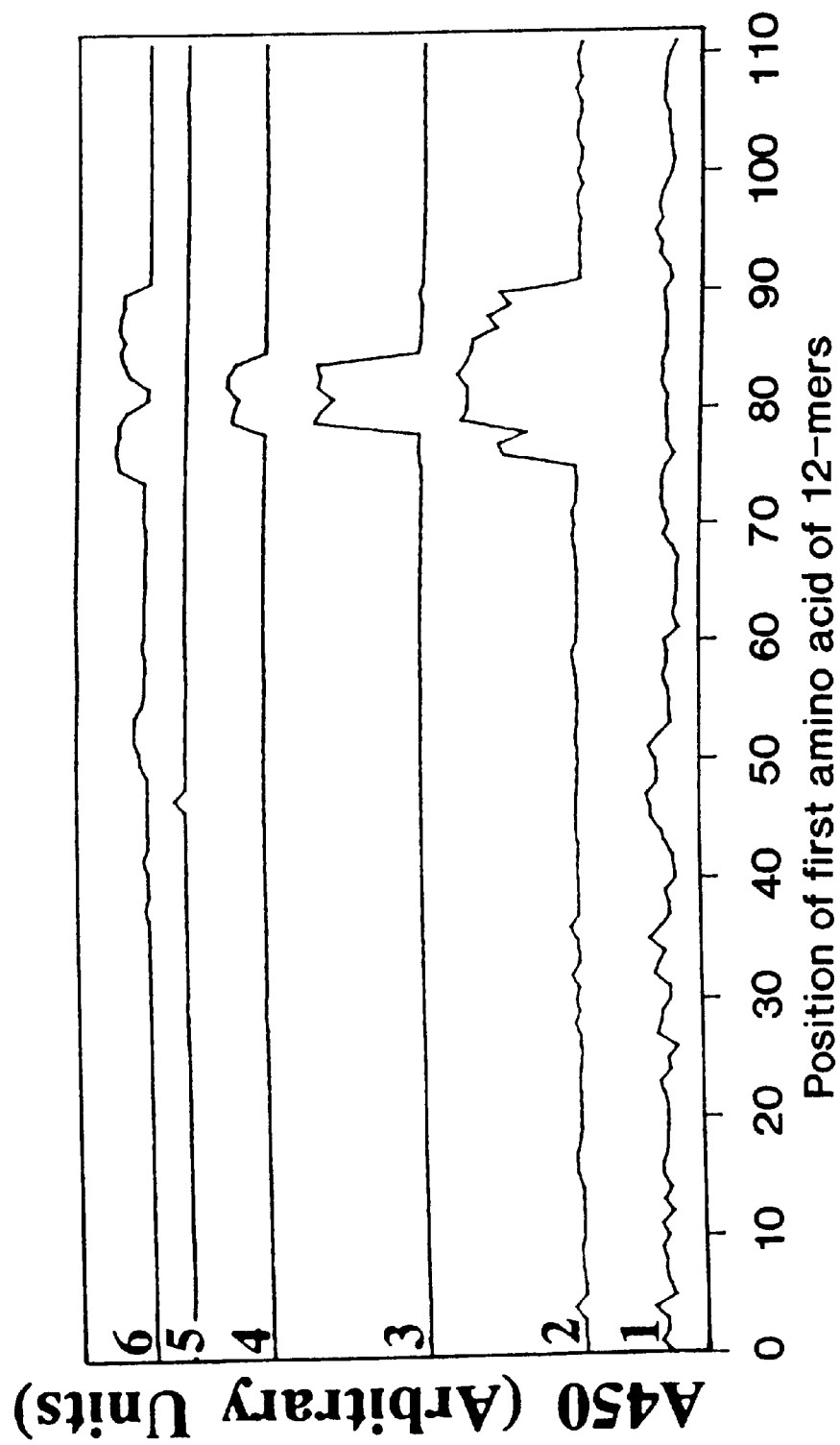

FIG. 3: results of PEPSCAN analysis using mouse monoclonal antibodies and rabbit sera.

Indicated on the X-axis are the relative starting positions of each individual 12-mer peptide on the EBNA-1 sequence, such that "0" represents the 12-mer peptide starting at AA 348 and so forth. Indicated on the Y-axis are relative absorbance units at 450 nm.

Line 1 represents the reactivity of an anti EBV VCA p40 monoclonal (EBV.OT41A) towards the EBNA-1 derived peptides, used as negative control.

Line 2–4 represent the reactivity of the anti EBNA-1 mouse monoclonal antibody EBNA.OT1x in different concentrations (5 μg/ml, long/ml and 1 ng/ml respectively).

Line 5 represents the reactivity of non-immunized rabbit serum.

Line 6 indicates the reactivity of rabbit serum immunized with recombinant EBNA-1.

FIG. 4: Indirect immunofluorescence for the detection of EBNA-1 in EBV-infected cells using the EBNA.OT1x monoclonal antibody. A: X50-7 cells, latently infected with EBV. B: HH514.c16 cells induced for EBV expression mixed 1:1 with EBV negative BJAB cells.

FIG. 5: FACS analysis of intranuclear EBNA-1 staining in a variety of lymphoid cells and cell lines:

A: Analysis of EBV negative Jurkat cells,

B: Analysis of EBV positive human Burkitt lymphoma cells (Daudi),

C: Analysis of peripheral blood lymphocytes from an EBV seronegative donor.

D: Analysis of polyclonal EBV transformed human B-lymphocytes,

E and F: Analysis of established cloned B-cells (EBV-positive).

The Y-axis represents the number of cells counted, while the X-axis represents the fluorescence intensity per cell.

The dotted line in each graph represents the control antibody (anti HIV-p24).

FIG. 6:

A: Results of EBNO typing of different EBV strains with monoclonal antibody EBNA.OT1x.
B: Results of EBNO typing of different EBV strains with human serum.
1=BJAB
2=CR+B95.8
3=CR+QIMR-WIL
4=PB-LCL
5=CR+BL72
6=CR+Mwika
7=CR+AG876
8=CR+Ambobi
9=CR+WW1
10=CR+WW2

The invention is further exemplified by the following examples:

EXAMPLE 1

Localisation of immunoreactive domains by PEPSCAN

Peptides with a length of 12 amino acids (AA) and an overlap of 11 AA of the AA sequence of ORF $BKRF_1$, positions 348–470 [SEQ ID NO: 1], were synthesized by automated solid phase peptide synthesis onto chemically activated polyethylene pins as originally described by Geijsen et al. (P.N.A.S., USA, 83, 3998–4002, 1984).

Figure 1:
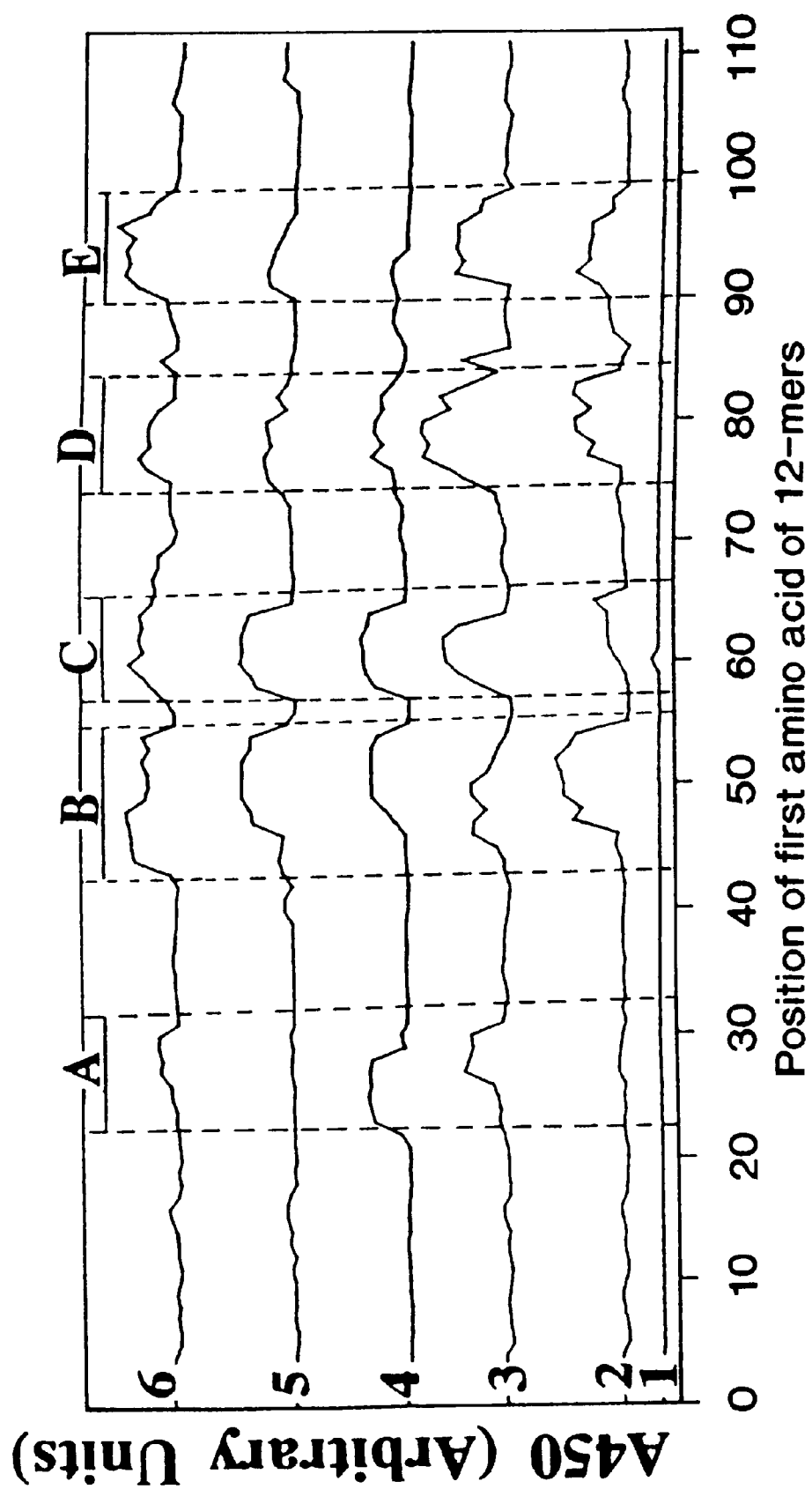
FIG. 1: results of PEPSCAN analysis with human sera. Indicated on the X-axis are the relative starting positions of each individual 12-mer peptide on the EBNA-1 sequence, such that "0" represents the 12-mer peptide starting at AA 348 and so forth. Indicated on the Y-axis are relative absorbance units at 450 nm.

The immunoreactivity for EBV-specific antibodies was determined as described by Middeldorp and Meloen (J.virol. Meth.21, 147–159, 1988). The results of such a PEPSCAN analysis for 6 individual human sera is shown in FIG. 1.

From this figure it can be seen that reactive regions are found with 12-mer peptides starting at AA20–31, 43–65, 74–85 and 90–98, representing AA 372–381, 391–413, 422–433 and 438–446 on the EBNA-1 sequence respectively. Similar reactivities were found with additional sets of human sera. No significant reaction was found when using EBV-seronegative sera, as indicated by line no.1 in FIG. 1.

EXAMPLE 2

Selection of immunoreactive synthetic peptides

The selection of synthetic peptides, derived from the $BKRF_1$-encoded EBNA-1 protein by computer analysis and PEPSCAN, and the analysis of the immunoreactivity of these peptides with normal human donor sera is outlined below.

Synthetic peptides were made by standard solid phase synthesis using t-BOC chemistry. Peptides from the AA 348–470 [SEQ ID NO: 1] fragment of the $BKRF_1$-encoded EBNA-3 protein were selected either on the basis of predicted high antigenicity using the computer program "antigenic index" developed by Jameson and Wolf (CABIOS 4, 181–186, 1988) [peptides 348–369 and 368–387 were selected on this basis] or on the basis of functional high antigen reactivity in PEPSCAN as described in Example 1 [Peptides 394–420 and 424–452] were selected on this basis.

In addition, a combi-peptide was made which represents a combination of the four most reactive domains (B–E in FIG. 1) identified by PEPSCAN. The sequence of this combi-peptide is depicted in SEQ ID. No.: 5.

For control purposes the P107 glycine-alanine co-polymer peptide was used as described by A.Linde et al. (J.Infect. Dis., 161, 903–910, 1990). This peptide represents a previously published immunoreactive domain of the EBNA-1 protein. In addition, a recombinant form of the EBNA-1 protein, containing the full length EBNA-1 sequence except the glycine-alanine domain was used. This recombinant protein was purified from rec. Baculovirus-infected insect cells as described by Frappier and O'Donnell (J.Biol.Chem., 266, 7819–7826, 1991).

The peptides and proteins described above were coated onto the solid phase; the wells of polystyrene microtiter plates, at 1 μg per ml. in 0,05M $NaHCO_3$ buffer of pH 9.6 overnight at 4° C. After washing twice with phosphate-buffered saline at pH 7.4 (PBS) the wells were filled with 100 μl of human serum, diluted 1:100 in PBS containing 0.05% Tween-20 (PBST) and incubated for 1 hour at 37° C. After three PBST washes HRP-labelled sheep anti-human IgG antibodies were added at the appropriate dilution in PBST and incubated for 1 hour at 37° C. After three washes with PBST, bound enzyme activity was detected using TMB as substrate. The reaction was stopped at 30 minutes by adding 100 μl 1M $H_2SO_4$. The absorbance was measured at 450 nm using a Multiscan photometer. Sera were tested for the presence of EBV antibodies using standard immunofluorescence serology or immunoblot analysis as described by Middeldorp and Herbrink (J.Virol.Meth., 21, 133–146, 1988).

FIG. 2 shows the results of ELISA experiments using the respective EBNA-1 reagents coated on the solid phase and a panel of 36 EBV-seropositive sera (□) and 10 EBV-seronegative sera (Δ). From this figure it can be seen that sera that contained no detectable antibodies to EBNA-1 by immunoblot were negative with all EBNA derived peptides except with the combi-peptide and the Baculo-derived EBNA-1 protein.

From the above described experiments it is apparent that computer predictions based upon the "antigenic index" program have no predictive value with respect to the immunogenecity towards sera from naturally infected individuals as almost all sera are negative with the highly charged peptides 348–369 and 368–387.

Peptides selected on the basis of PEPSCAN show good reactivity with 80–90% of the sera for peptides 394–420 (combination of domains B+C of FIG. 1) and 424–452 (combination of domain D+E). Surprisingly the combi-peptide shows positive reactivity with 100% of the EBV-seropositive sera tested. EBV seronegative sera show no reactivity with the combi-peptide, whereas one such serum showed a false-positive reaction with the baculo derived EBNA-1 protein.

EXAMPLE 3

Localization of immunoreactive epitopes on EBNA-1 using mouse monoclonal antibodies.

The procedure used for the localization of immunoreactive epitopes on EBNA-1 fragment 348–470 using mouse monoclonal antibodies and rabbit sera are as already described in Example 1 for the localization of epitopes using human sera.

Mouse antibody-binding to the pin-bound peptides was measured using sheep anti-mouse IgG labelled with peroxidase, whereas rabbit antibody binding was measured using sheep anti-rabbit labelled with peroxidase.

Results are shown in FIG. 3. From these results it can be seen that monoclonal antibodies not specifically directed at EBNA proteins (anti EBV VCA-p40 or non-immunized rabbit serum) do not react with any of the EBNA-1 peptides tested.

Mouse monoclonal EBNA.OT1x recognizes an epitope at AA420–445 when used at high concentration, which narrows down with dilution of the antibody to an epitope at AA430–438. The rabbit serum 121-3, raised by immunization with the Baculo derived EBNA-1 protein, recognizes three epitopes in the EBNA-1 region analysed.

EXAMPLE 4

Indirect immunofluorescence for the detection of EBNA-1 in EBV-infected cells, using EBNA.OT1x A. X50-7 cells, latently infected with EBV, were fixed with acetone-methanol (1:1) on 12 well glass slides stained with EBNA.OT1x antibody at 24 g/ml in phosphate buffered saline pH 7.4 (PBS) containing 1% Bovine Serum Albumin (BSA) for 1 hour at $37_oC$. After four PBS washes rabbit anti-mouse IgG labelled with fluorescein isothiocyanate (FITC) was added, diluted in PBS-1% BSA and incubated for 1 hour at $37_oC$. After four additional PBS washes goat anti-rabbit labelled with FITC was added and incubated as above. Finally, after four PBS washes, the slides were covered with mounting fluid (50% glycerol pH9.0) and sealed with a cover slip.

B: HH514.c16 cells, a superinducible clone from the EBV-producer cell line $P_3HR_1$, induced for EBV-expression using TPA and butyrate for 6 days were mixed 1:1 with EBV-negative BJAB cells and fixed onto 12-well glass slides using 100% acetone. EBNA.OT1x was added as described under A and after four washes with PBS goat anti-mouse F(ab)-FITC was added, appropriately diluted in PBS+1%BSA and incubated at 37° C. for 1 hour. After four PBS washes the slides were covered with mounting fluid and sealed with a cover slip.

All incubations (in A and B) were performed in a humidified chamber to prevent evaporation of reagents. Fluorescent staining was visualised using a Zeiss Axioscope fluorescence microscope (magnification 400x).

Figure 4A:
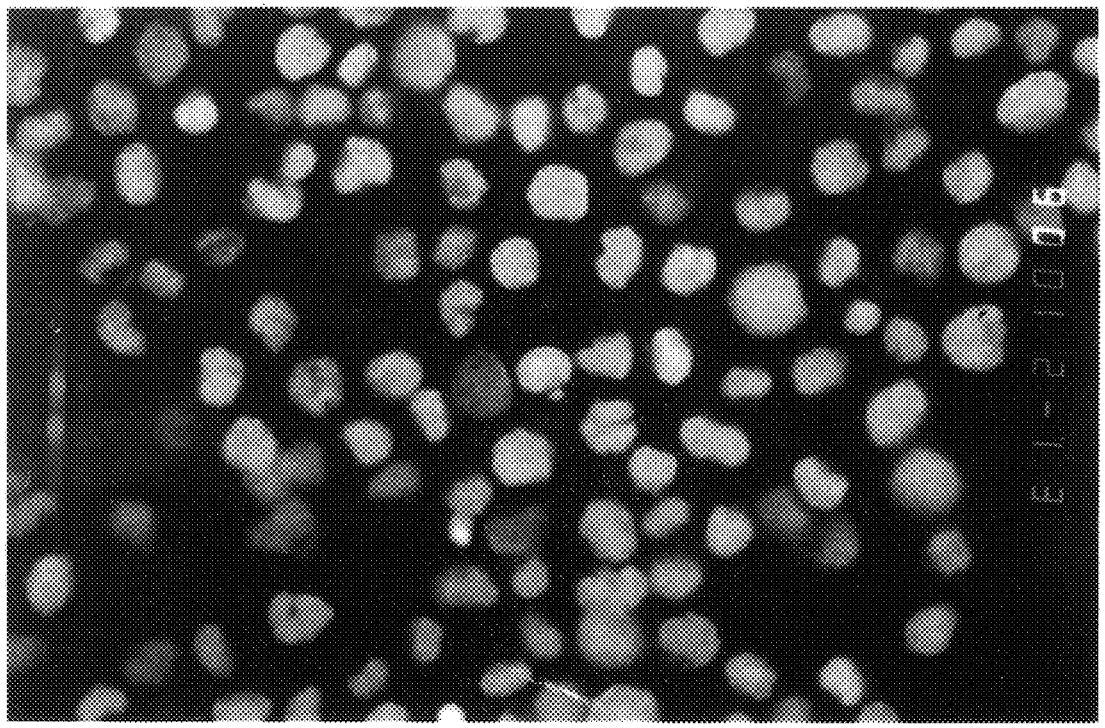
Figure 4B:
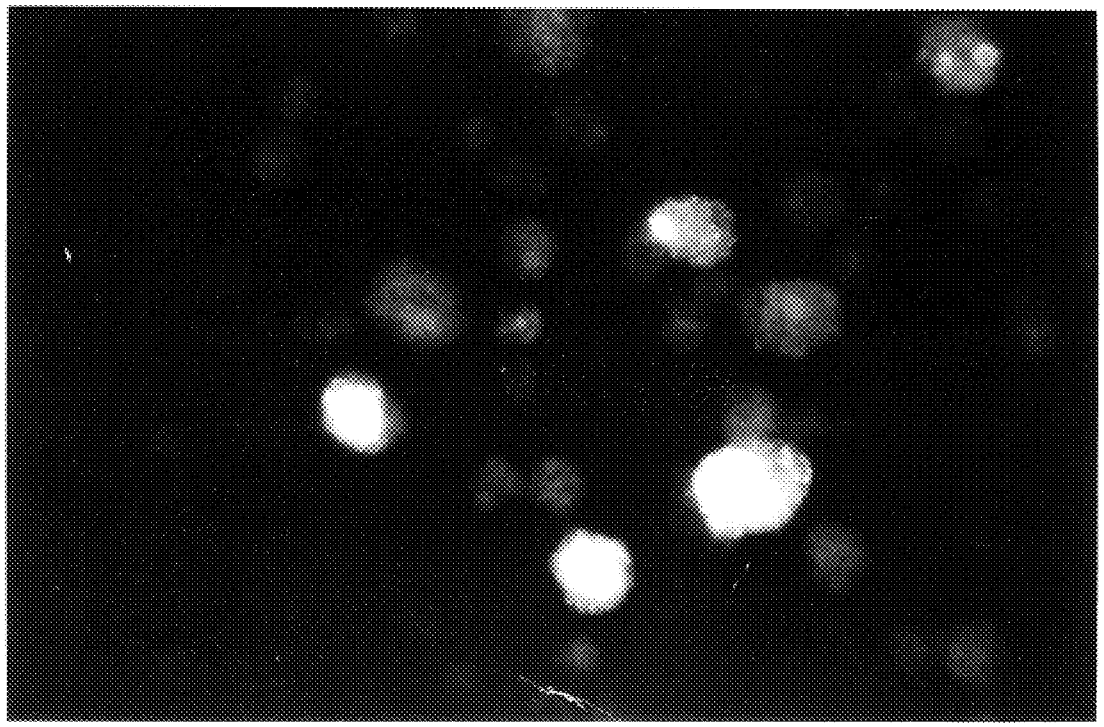
Figure 5B:
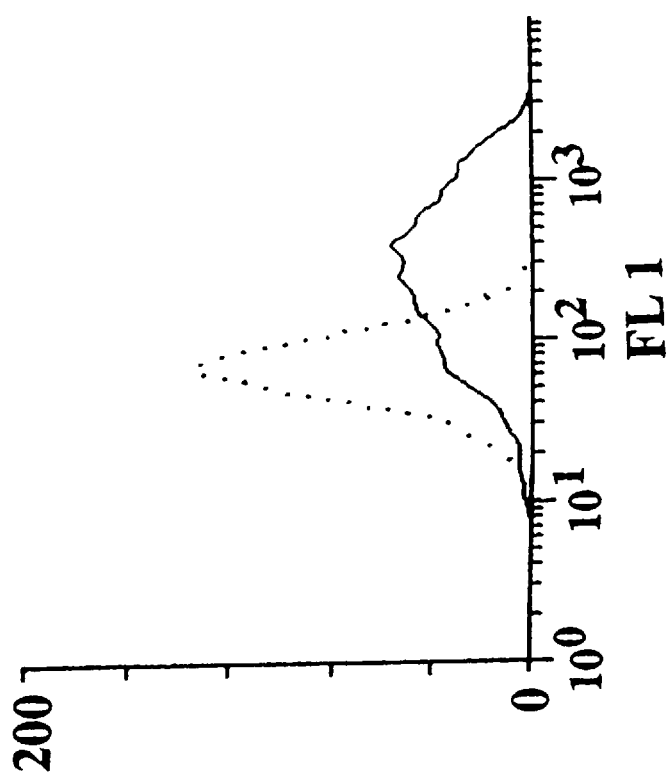
Figure 5A:
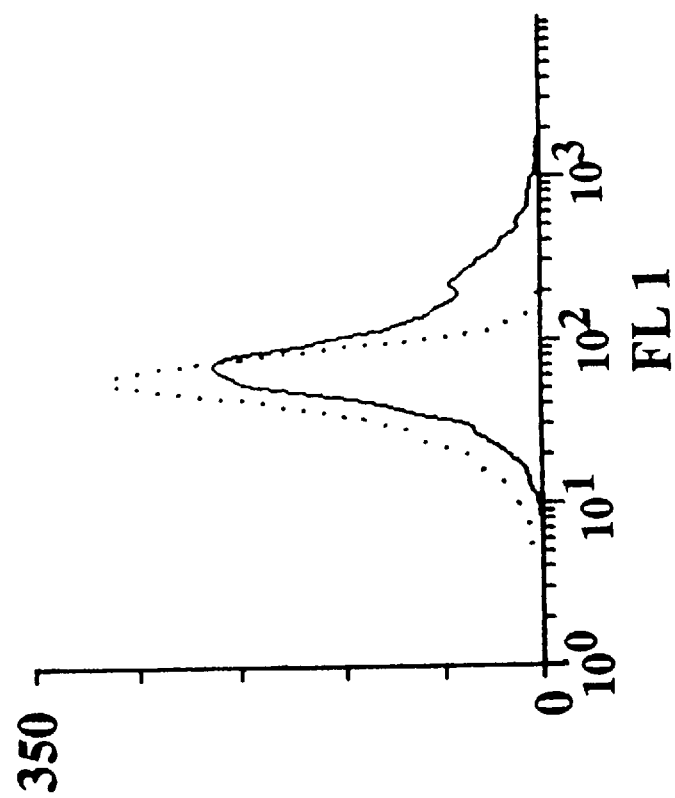
Figure 5D:
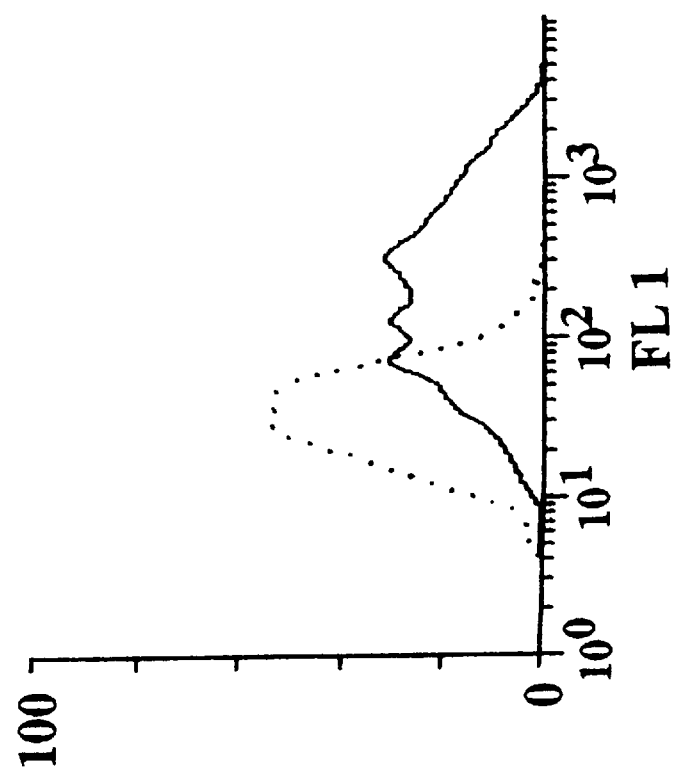
Figure 5C:
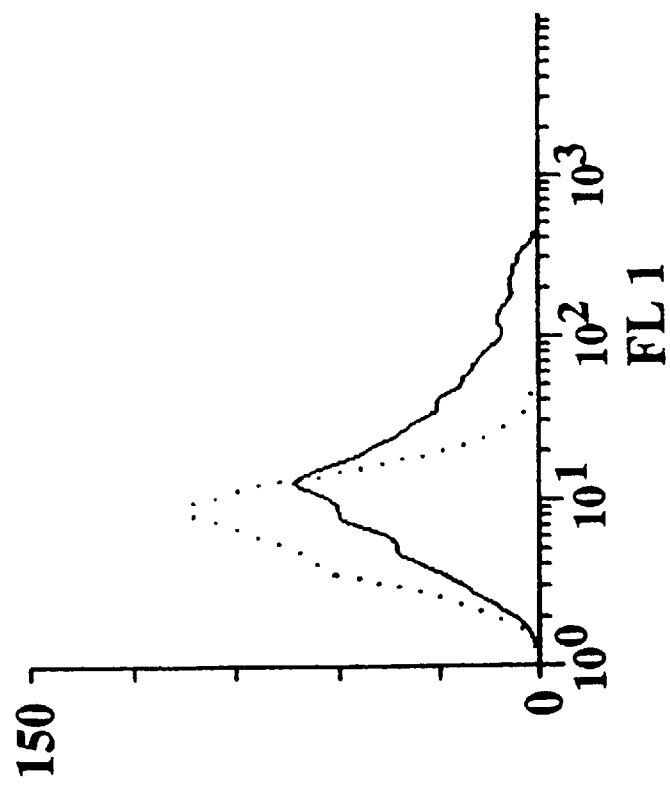

The results as depicted in FIG. 4A and 4B show a characterisitic nuclear EBNA staining pattern in 100% of the cells latently infected with EBV, such as found for the X50-7 cell line shown in panel A, when using a double FITC-staining technique, to increase sensitivity.

Results in panel B show the specificity of the staining by EBNA.OT1x as most of the small EBV-negative BJAB cells show no staining at all, whereas the large EBV-producer cells show a strong nuclear staining pattern in about 50% of the cells.

EXAMPLE 5

Fluorescence Activated Cell Sorter (FACS) analysis

EBV-negative human T-cells (Jurkat), EBV-positive human Burkitt-lymphoma cells (Daudi), polyclonal EBV-transformed human B-lymphocytes, established cloned B-cell lines or peripheral blood lymphocytes from an EBV-seronegative donor were fixed according to the BFA-method and incubated with EBNA.OT1x (1 µg/ml) in PBS plus 1% BSA at a cell concentration of $2 \times 10^6$/ml at 4° C.

After washing with PBS three times, the cells were incubated with goat anti-mouse IgG-F(ab)$_2$ labelled with FITC, appropriately diluted in PBS-BSA. After another wash step $10^4$ cells were analysed with a flow cytometer (FACSCAN, Becton-Dickinson). As a negative control each experiment was paralleled by a separate incubation of the same cells with a non-relevant monoclonal antibody (anti HIV-p24, IgG).

The results of the above described experiments are given in FIG. 5A–F. The dotted line in each graph represent the control monoclonal antibody whereas the continuous line shows the results obtained for the EBNA.OT1x monoclonal antibody. From these experiments it can be concluded that, using BFA as the fixation method as described by Slaper-Cortenbach et al. (Blood, 72, 1639–1644, 1988), EBNA.OT1x is capable of penetrating into cells thus allowing the detection of EBNA-1 intracellularly in EBV-infected cells.

EXAMPLE 6

Immunoblot staining and EBNO typing.

The detection of denatured EBNA-1 by means of immunoblot staining and its application in EBNO-typing of different EBV isolates using the EBNA.OT1x antibody according to the invention is illustrated below.

In FIG. 6 an example is shown of an analysis with a variety of different EBV strains as present in B-cell lines obtained from different geographical regions in the world.

Figure 6A:
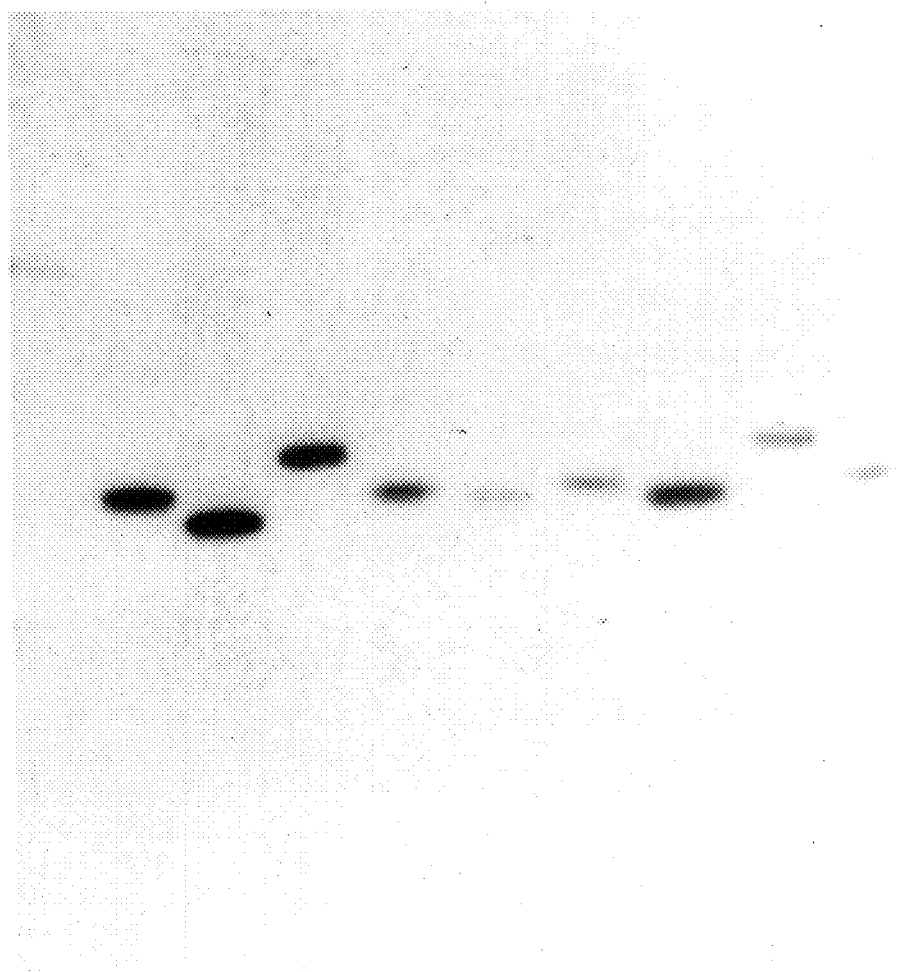
Figure 6B:
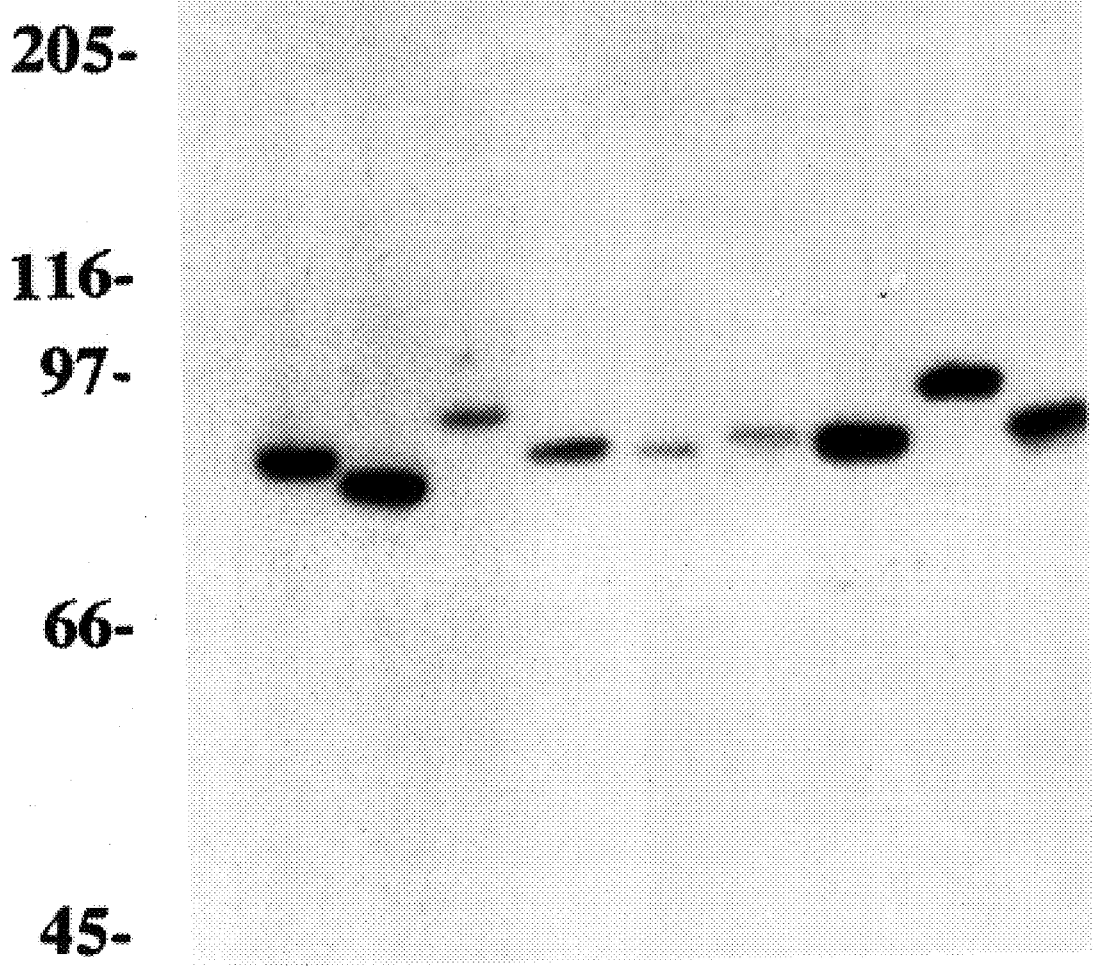

In each line of FIG. 6A and 6B a sample of $5 \times 10^4$ EBV-infected or control (BJAB) cells, denatured by boiling in reducing SDS-PAGE sample buffer, was subjected to standard SDS-PAGE and blotting to nitro cellulose.

Panel A (FIG. 6A) shows the EBNA-staining using EBNA.OT1x monoclonal antibody whereas panel B shows the same analysis using a human serum mono-specific for EBNA-1 staining (i.e. not reactive with additional EBNA molecules). In spite of the differences in intensity, the staining patterns for both reagents are identical, showing the molecular weight variation among individual EBV-isolates. BJAB represents an EBV-negative cell line extract.

From these experiments it can be concluded that EBNA.OT1x reacts with multiple EBV-strains and can be used as reagent in EBNO-typing.

I claim:

1. A peptide comprising one or more of the amino acid sequences selected from the group consisting of SEQ ID NOs: 3, 4, 5 and 6, provided that said peptide does not contain any amino acid sequence of EBNA-1 of Epstein-Barr Virus, EBV, other than the sequences of SEQ ID NOs: 3, 4, 5 and 6.

2. An immunochemical reagent comprising a peptide according to claim 1 bound to a support or label.

3. A method for the detection of antibodies directed against EBV in a test fluid, comprising bringing the immunochemical reagent according to claim 2 into contact with the test fluid and detecting the presence of immune complexes formed in the test fluid, whereby the presence of immune complexes indicates the presence of EBV antibodies in said sample.

4. A method for the detection of Epstein-Barr Virus in a test fluid, comprising bringing the immunochemical reagent according to claim 2 into contact with the test fluid and antibodies directed against Epstein-Barr Virus, and detecting the presence of immune complexes formed, whereby the presence of Epstein-Barr Virus in the test fluid is determined.

5. A test kit, comprising a peptide according to claim 1, wherein said peptide is bound to a support or label.

6. The test kit of claim 5, further comprising a labeled antibody that will specifically bind said peptide.

7. The peptide of claim 1, which is fused to a heterologous peptide.

8. An isolated and purified antibody that will specifically bind a peptide according to claim 1.

9. An immunochemical reagent comprising an antibody according to claim 8, bound to a support or label.

10. A method for detection of EBV in a sample which comprises contacting said sample with an antibody according to claim 8, and detecting the presence of immune complexes formed, whereby the presence of EBV in the sample is determined by the presence of said immune complexes.

11. A test kit, comprising an antibody according to claim 8.

12. The antibody according to claim 8, which is a monoclonal antibody.

13. A monoclonal antibody that specifically binds the same epitope on EBNA-1 as monoclonal antibodies produced by the hybridoma cell line deposited with the European Collection of Animal Cell Cultures (ECACC), Porton Down (UK), under deposit No. 92071613.

14. An immortalized cell line capable of producing monoclonal antibodies according to claim 13.

15. An immortalized cell line deposited with the European Collection of Animal Cell Cultures (ECACC), Porton Down (UK), under deposit No. 92071613.

* * * * *